United States Patent
Sugiyama

(10) Patent No.: US 10,750,729 B2
(45) Date of Patent: Aug. 25, 2020

(54) PIG FOR ATRIOVENTRICULAR BLOCK MODEL, MONKEY FOR ATRIOVENTRICULAR BLOCK MODEL, GUINEA PIG FOR ATRIOVENTRICULAR BLOCK MODEL, AND USE THEREOF

(71) Applicant: Toho University, Tokyo (JP)

(72) Inventor: Atsushi Sugiyama, Tokyo (JP)

(73) Assignee: TOHO UNIVERSITY, Tokyo (JP)

( * ) Notice: Subject to any disclaimer, the term of this patent is extended or adjusted under 35 U.S.C. 154(b) by 1269 days.

(21) Appl. No.: 14/021,657

(22) Filed: Sep. 9, 2013

(65) Prior Publication Data

US 2014/0086841 A1 Mar. 27, 2014

(30) Foreign Application Priority Data

Sep. 24, 2012 (JP) .................................. 2012-209475

(51) Int. Cl.
*A01K 67/027* (2006.01)
*A61K 49/00* (2006.01)

(52) U.S. Cl.
CPC ........ *A01K 67/027* (2013.01); *A61K 49/0004* (2013.01); *A61K 49/0008* (2013.01)

(58) Field of Classification Search
None
See application file for complete search history.

(56) References Cited

PUBLICATIONS

Assessment Report-Gilenya, "Assessment Report-Gilenya", EMA, 2011, pp. 1-117.*
Takasuna, K., et al., "Pre-clinical QT Risk Assessment in Pharmaceutical Companies—Issues of Current QT Risk Assessment", Biomolecules and Therapeuticsm 2009, pp. 1-11.*
Authier, S., et al., "A cardiovascular monitoring system used in conscious cynomolgus monkeys for regulatory safety pharmacology: Part 2: Pharmacological validation", J. Pharm. and Tox. Meth., 2007, pp. 122-130.*
Belardinelli, L., et al., "Atrioventricular Conduction Disturbances during Hypoxia", Circulation Research, 1980, pp. 684-691.*
Sakaguchi, Y., et al., "Halothane-Anaesthetized, Closed-Chest, Guinea-Pig Model for Assessment of Drug-Induced QT-Interval Prolongation", Basic and Clinical Pharmacology and Toxicology, 2008, pp. 43-48 (Year: 2008).*
Lu, H.R., et al., "Inhibition of Na+/Ca2+ overload with R56865 protects against cardiac arrhythmias elicited by ouabain in vivo in guinea-pigs", European Journal of Pharmacology, pp. 89-93 (Year: 1993).*
Ich Guidelines, "The Non-Clinical Evaluation of the Potential for Delayed Ventricular Repolarization (QT Interval Prolongation) by Human Pharmaceuticals", ICH, pp. 1-10 (Year: 2005).*
Office Action in the corresponding Japanese Application No. 2012-209475 dated Apr. 5, 2016 (9 pages).
Pilote et al.: "A new oral treatment for relapsing forms of multiple sclerosis, causes bradycardia and prolongs the QTC interval"; Canadian Journal of cardiology, 2012, vol. 28, pp. 2-4.
Atsushi Sugiyama: "Drug-induced Cardiotoxicity: Translational Research from Animal to Human"; Department of Pharmacology, School of Medicine, Toho University, 2012. (English translation).
Sugiyama et al.: "Non-clinical Toxicity test using Pig, Development of Chronic Atrioventricular Block Model using Mircrominipig (Durg-induced Fatal Arrhuthmia prediction model)" Department of Pharmacology, School of Medicine, Toho University, 2011 (English translation).
"Therapeutic drug for Multiple Sclerosis Imusera (registered trademark) capsule 0.5 mg," Pharmaceutical Interview Form, revised in Apr. 2012 (third edition), 122 pages total (English translation provided).
Sugiyama et al., "Effects of sphingosine I-phosphate, a naturally occurring biologically active lysophospholipid, on the rat cardiovascular system," Jpn. J. Pharmacol., 2000, 82(4), pp. 338-342.

* cited by examiner

*Primary Examiner* — Michael G. Hartley
*Assistant Examiner* — Lance W Rider
(74) *Attorney, Agent, or Firm* — Hamre, Schumann, Mueller & Larson, P.C.

(57) ABSTRACT

A method for allowing an animal to develop atrioventricular block, the method including: administering an immune regulator targeting a sphingosine-1-phosphate receptor to an animal selected from a pig, a monkey and a guinea pig.

1 Claim, 8 Drawing Sheets

Base control (before drug administration)

50 min after drug administration

Base control
(before drug administration)

45 min after the start of high-dose drug administration

Base control
(before drug administration)

45 min after the start of high-dose drug administration

PIG FOR ATRIOVENTRICULAR BLOCK MODEL, MONKEY FOR ATRIOVENTRICULAR BLOCK MODEL, GUINEA PIG FOR ATRIOVENTRICULAR BLOCK MODEL, AND USE THEREOF

BACKGROUND OF THE INVENTION

Field of the Invention

The present invention relates to a pig for an atrioventricular block model, a monkey for an atrioventricular block model, a guinea pig for an atrioventricular block model, a method for allowing a pig, a monkey or a guinea pig to develop atrioventricular block, an evaluation method for evaluating development of atrioventricular block, an atrioventricular block model, and a method for producing the atrioventricular block model.

Description of the Related Art

Fingolimod (also called "FTY720") [trade name: IMUSERA (registered trademark, product of Mitsubishi Tanabe Pharma Corporation (see "Therapeutic Drug for Multiple Sclerosis IMUSERA (registered trademark) capsule 0.5 mg" Pharmaceutical Interview Form, revised in April, 2012 (third edition)) or trade name: GILENYA (Novartis Pharma K.K.)) is a drug for multiple sclerosis targeting a sphingosine-1-phosphate receptor. At the 3rd DIA Cardiac Safety Workshop (May 28, 2012, Tokyo), Dr. Strnadova (Health Canada, Canada) reported that fingolimod was administered to 366 cases at a dose of 1.25 mg/day in a clinical trial (phase III) and the Holter electrocardiograms measured one day after the administration thereof show that 6.6% of the cases developed second-degree atrioventricular block (Mobitz type I or type II), 3.4% thereof developed advanced atrioventricular block (2:1 atrioventricular block) and 0.3% thereof developed third-degree atrioventricular block (complete atrioventricular block). Although the frequency of occurrence of complete atrioventricular block is quite low, fingolimod causes complete atrioventricular block one day after the administration thereof and has a risk of causing sudden death. Thus, fingolimod is quite dangerous and has problems to be solved rapidly.

Notably, the safety of fingolimod was evaluated in a non-clinical trial by administering fingolimod to experimental animals such as a mouse and a dog at a dose 10 times to 30 times greater than that for human, and as a result the occurrence of atrioventricular block was not reported in these animals but was confirmed for the first time when fingolimod was administered to human.

Also, it has been reported that prolongation of PR interval was not observed when administering sphingosine-1-phosphate to a rat (see Sugiyama A, et al., 2000, Jpn. J. Pharmacol., 82(4), pp. 338-342).

The atrioventricular block is a type of arrhythmia and includes first-degree atrioventricular block, second-degree atrioventricular block, advanced atrioventricular block, and third-degree atrioventricular block. The first-degree atrioventricular block is a state where PR interval is prolonged for 0.2 sec or longer in human. The second-degree atrioventricular block is further classified into Type 1 (Mobitz type I (also called "Wenckebach type")) and Type 2 (Mobitz type II). The Wenckebach type is a state of repeating a pattern where PR interval is gradually prolonged and then QRS (ventricular contraction) is dropped. The Mobitz type II is a state where ventricular contraction is suddenly dropped without prolongation of PR interval. The advanced atrioventricular block is a state where atrial excitation is conducted to the ventricle at a frequency of only 2:1 (atrium:ventricle) or 3:1 (atrium:ventricle) or less. The third-degree atrioventricular block is a state where the atrium and the ventricle are moved independently of each other at their own individual rhythms.

Fingolimod is one example of a commercially available drug having a side effect of fatal ventricular arrhythmia which could not be predicted in its non-clinical trial. Similar to fingolimod, all immune regulators targeting a sphingosine-1-phosphate receptor have a risk that the occurrence of atrioventricular block is first confirmed although such a side effect of causing atrioventricular block was not confirmed in their non-clinical trials.

Therefore, at present, there has been a strong demand to predict development of atrioventricular block as a side effect at the stage of non-clinical trials, in order to eliminate possibility of sudden death caused by complete atrioventricular block and further develop an immune regulator capable of being conveniently administered to patients at their homes rather than under medial supervision.

SUMMARY OF THE INVENTION

The present invention aims to solve the above existing problems and achieve the following object. That is, an object of the present invention is to provide: a pig for an atrioventricular block model, a monkey for an atrioventricular block model, and a guinea pig for an atrioventricular block model, which are for predicting development of atrioventricular block caused by a drug at the stage of non-clinical trials; a method for allowing a pig, a monkey or a guinea pig to develop atrioventricular block; an evaluation method for efficiently and conveniently evaluating development of atrioventricular block; an atrioventricular block model which can be used for analysis of pathological condition of atrioventricular block; and a method for producing the atrioventricular block model.

The present inventors conducted extensive studies to solve the above problems and as a result have obtained the following finding. That is, use of a pig, a monkey, a guinea pig, or any combination thereof can surely predict development of atrioventricular block caused by an immune regulator targeting a sphingosine-1-phosphate receptor. The present invention has been completed on the basis of this finding.

The present invention is based on the above finding obtained by the present inventors, and means for solving the above problems are as follows.

That is, a method of the present invention for allowing an animal to develop atrioventricular block includes administering an immune regulator targeting a sphingosine-1-phosphate receptor to an animal selected from a pig, a monkey and a guinea pig.

A method of the present invention for producing an atrioventricular block model includes administering an immune regulator targeting a sphingosine-1-phosphate receptor to an animal selected from a pig, a monkey and a guinea pig.

A pig of the present invention for an atrioventricular block model is a pig that is used for production of an atrioventricular block model.

An atrioventricular block model of the present invention is an atrioventricular block model of a pig.

A monkey of the present invention for an atrioventricular block model is a monkey that is used for production of an atrioventricular block model.

An atrioventricular block model of the present invention is an atrioventricular block model of a monkey.

A guinea pig of the present invention for an atrioventricular block model is a guinea pig that is used for production of an atrioventricular block model.

An atrioventricular block model of the present invention is an atrioventricular block model of a guinea pig.

An evaluation method of the present invention includes evaluating development of atrioventricular block caused by an immune regulator targeting a sphingosine-1-phosphate receptor with a pig, a monkey, a guinea pig, or any combination thereof.

The present invention can solve the above existing problems and achieve the above object, providing: a pig for an atrioventricular block model, a monkey for an atrioventricular block model, and a guinea pig for an atrioventricular block model, which are for predicting development of atrioventricular block caused by a drug at the stage of non-clinical trials; a method for allowing a pig, a monkey or a guinea pig to develop atrioventricular block; an evaluation method for efficiently and conveniently evaluating development of atrioventricular block; an atrioventricular block model which can be used for analysis of pathological condition of atrioventricular block; and a method for producing the atrioventricular block model.

Figure 1A:
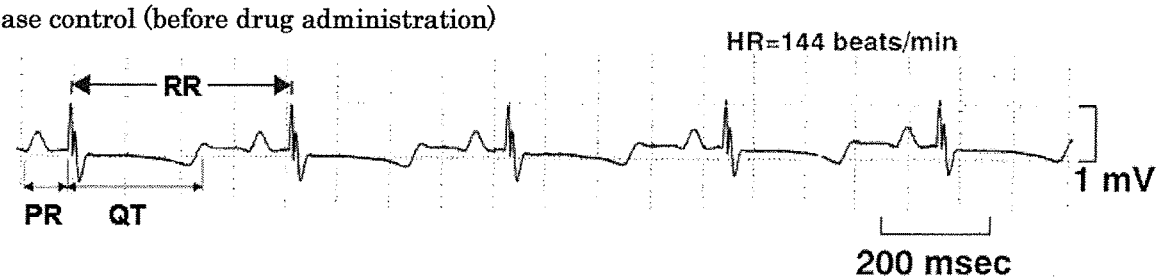
FIG. 1A shows one exemplary trace of an electrocardiogram of a pig before drug administration in Test Example 1.

DETAILED DESCRIPTION OF THE INVENTION (Pig for an Atrioventricular Block Model, Monkey for an Atrioventricular Block Model, or Guinea Pig for an Atrioventricular Block Model)

A pig of the present invention for an atrioventricular block model is a pig that is used for production of an atrioventricular block model.

A monkey of the present invention for an atrioventricular block model is a monkey that is used for production of an atrioventricular block model.

A guinea pig of the present invention for an atrioventricular block model is a guinea pig that is used for production of an atrioventricular block model.

<Pig>

The body weight, age, sex, etc. of the pig are not particularly limited and may be appropriately selected depending on the intended purpose.

The type of the pig is also not particularly limited and may be appropriately selected depending on the intended purpose. The pig is preferably an extremely small-size miniature pig having a body weight of 10 kg or less from the viewpoint of easy handling as an experimental animal. The extremely small-size miniature pig having a body weight of 10 kg or less is available from Fuji Micra Inc. (trade name: Microminipig).

When an immune regulator targeting the sphingosine-1-phosphate receptor is administered to the pig for an atrioventricular block model, it causes prolongation of electrophysiological parameters in an electrocardiogram (e.g., PR interval and AH interval). Thus, at the stage of non-clinical trials, the pig for an atrioventricular block model can suitably be used for evaluation of a risk of development of first-degree atrioventricular block.

<Monkey>

The type, body weight, age, sex, etc. of the monkey are not particularly limited and may be appropriately selected depending on the intended purpose.

When an immune regulator targeting the sphingosine-1-phosphate receptor is administered to the monkey for an atrioventricular block model, it causes prolongation of electrophysiological parameters in an electrocardiogram (e.g., PR interval and AH interval). Thus, at the stage of non-clinical trials, the monkey for an atrioventricular block model can suitably be used for evaluation of a risk of development of first-degree atrioventricular block.

<Guinea Pig>

The type, body weight, age, sex, etc. of the guinea pig are not particularly limited and may be appropriately selected depending on the intended purpose.

When an immune regulator targeting the sphingosine-1-phosphate receptor is administered to the guinea pig for an atrioventricular block model, it causes not only prolongation of electrophysiological parameters in an electrocardiogram (e.g., PR interval and AH interval) but also develops complete atrioventricular block. Thus, at the stage of non-clinical trials, the guinea pig for an atrioventricular block model can suitably be used for evaluation of not only a risk of development of first-degree atrioventricular block but also risks of development of second-degree atrioventricular block, advanced atrioventricular block and third-degree atrioventricular block.

The sphingosine-1-phosphate receptor is expressed in many immunocytes such as T cells, mast cells, macrophages, dendritic cells and NK cells. When sphingosine-1-phosphate binds to the sphingosine-1-phosphate receptor, cell migration and other responses are caused to evoke immune activity.

The immune regulator targeting the sphingosine-1-phosphate receptor binds to the sphingosine-1-phosphate receptor to serve as a functional antagonist for the sphingosine-1-phosphate receptor, suppressing the effects by the sphingosine-1-phosphate.

The pig for an atrioventricular block model, the monkey for an atrioventricular block model, or the guinea pig for an atrioventricular block model can suitably be used for evaluation of a risk of development of atrioventricular block in all of the immune regulators targeting the sphingosine-1-phosphate receptor.

(Method for Allowing an Animal to Develop Atrioventricular Block)

A method of the present invention for allowing an animal to develop atrioventricular block includes: an administering step; and, if necessary, further includes other steps such as an anesthetizing step.

The animal is selected from a pig, a monkey and a guinea pig.

<Administering Step>

The administering step is a step of administering an immune regulator targeting a sphingosine-1-phosphate receptor to an animal.

The body weight, age, sex, etc. of the pig are not particularly limited and may be appropriately selected depending on the intended purpose.

The type of the pig is also not particularly limited and may be appropriately selected depending on the intended purpose. The pig is preferably the above-described extremely small-size miniature pig from the viewpoint of easy handling as an experimental animal.

The type, body weight, age, sex, etc. of the monkey are not particularly limited and may be appropriately selected depending on the intended purpose.

The type, body weight, age, sex, etc. of the guinea pig are not particularly limited and may be appropriately selected depending on the intended purpose.

The immune regulator is not particularly limited and may be appropriately selected depending on the intended purpose so long as it targets a sphingosine-1-phosphate receptor. Examples thereof include fingolimod (FTY720) and siponimod (BAF312). These may be used alone or in combination.

A method for administering the immune regulator is not particularly limited and may be appropriately selected depending on the intended purpose. It is preferably intravenous administration from the viewpoint of surely making a drug reach circulating blood.

A dose of the immune regulator is not particularly limited and may be appropriately selected depending on the intended purpose.

When the immune regulator is fingolimod, the dose thereof is preferably at least 0.1 mg/kg. When the dose is less than 0.1 mg/kg, there may be a case where atrioventricular block is not developed.

When the immune regulator is siponimod, the dose thereof is preferably at least 0.01 mg/kg. When the dose is less than 0.01 mg/kg, there may be a case where atrioventricular block is not developed.

<Anesthetizing Step>

The anesthetizing step is a step of anesthetizing an animal. The anesthetizing step is preferably performed before the administering step.

The type of an anesthetic drug used in the anesthetizing step is not particularly limited and may be appropriately selected depending on the intended purpose. Examples thereof include halothane, pentobarbital, thiopental, urethane, ketamine, chloral hydrate, tribromoethanol, phenothiazines, chlorpromazine, acepromazine, promazine, benzodiazepines, diazepam, midazolam, α-2adrenergic tranquilizers, xylazine and medetomidine. These may be used alone or in combination.

Among them, halothane is advantageously used since it can suppress transmission of electrical signals from the atrium to the ventricle of a pig, a monkey or a guinea pig to somewhat prolong the PR interval in advance, making it easier to produce an atrioventricular block model, especially a second- or third-degree atrioventricular block model.

A dose and an administration method of the anesthetic drug are particularly limited and may be appropriately selected depending on, for example, the type of the anesthetic drug and the type, body weight, age, sex, etc. of a target individual.

For example, as for halothane, it is preferred to allow the target individual to inhale vaporized halothane at a concentration of 1% by volume to 2% by volume.

In the anesthetizing step, it is preferred that in order to stabilize breathing of the target individual, a tube is inserted thereto and a certain amount of oxygen or air is supplied from an oxygen or air-supplying unit such as an artificial respirator.

An amount of the oxygen or air supplied is not particularly limited and may be appropriately selected depending on, for example, the body weight of the target individual, but is preferably 10 mL/kg to 20 mL/kg.

In particular, the amount of the oxygen or air supplied is preferably 10 mL/kg for a pig, preferably 20 mL/kg for a monkey, and preferably 10 mL/kg for a guinea pig.

(Evaluation Method)

An evaluation method of the present invention includes evaluating development of atrioventricular block caused by an immune regulator targeting a sphingosine-1-phosphate receptor with a pig, a monkey, a guinea pig, or any combination thereof.

In the evaluation method, all or one of the pig, the monkey and the guinea pig may be used, but preferably one or both of the pig and the monkey are used in combination with the guinea pig from the viewpoint of surely evaluating development of atrioventricular block. Particularly preferably, one or both of the pig and the monkey are used and then the guinea pig is used.

In general, in non-clinical trials of drugs, when there are concerns in safety to human even if no adverse side effects are observed in safety pharmacological studies evaluating adverse side effects and other properties, follow-up studies are performed for properly evaluating them.

The pig or the monkey is suitably used in a primary evaluating step as a core battery study, and the guinea pig is suitably used in a secondary evaluating step as a follow-up study.

<Primary Evaluating Step>

The primary evaluating step is a step of primarily evaluating the development of atrioventricular block caused by an immune regulator targeting a sphingosine-1-phosphate receptor with one or both of the pig and the monkey. The primary evaluating step can suitably evaluate a risk of development of first-degree atrioventricular block.

The body weight, age, sex, etc. of the pig are not particularly limited and may be appropriately selected depending on the intended purpose.

The type of the pig is also not particularly limited and may be appropriately selected depending on the intended purpose. The pig is preferably the above-described extremely small-size miniature pig from the viewpoint of easy handling as an experimental animal.

The type, body weight, age, sex, etc. of the monkey are not particularly limited and may be appropriately selected depending on the intended purpose.

An evaluation method in the primary evaluating step is not particularly limited and may be appropriately selected depending on the intended purpose. Examples thereof include a method of measuring an electrocardiogram and evaluating presence or absence of prolongation of electrophysiological parameters (e.g., PR interval and AH interval).

<Secondary Evaluating Step>

The secondary evaluating step is a step of secondarily evaluating the development of atrioventricular block caused by an immune regulator targeting a sphingosine-1-phosphate receptor with the guinea pig.

The secondary evaluating step can suitably evaluate risks of development of second- and third-degree atrioventricular block in addition to the risk of development of first-degree atrioventricular block.

The type, body weight, age, sex, etc. of the guinea pig are not particularly limited and may be appropriately selected depending on the intended purpose.

An evaluation method in the secondary evaluating step is not particularly limited and may be appropriately selected depending on the intended purpose. Examples thereof include: a method of measuring an electrocardiogram and evaluating presence or absence of prolongation of electrophysiological parameters (e.g., PR interval and AH interval); and a method of evaluating an electrocardiogram for presence or absence of development of second- and/or third-degree atrioventricular block.

The evaluation method can suitably be used for predicting development of atrioventricular block caused by an immune regulator targeting a sphingosine-1-phosphate receptor at the stage of non-clinical trials.

(Atrioventricular Block Model)

An atrioventricular block model of the present invention is a pig, a monkey or a guinea pig. The atrioventricular block model is a model which develops atrioventricular block.

<Pig>

The body weight, age, sex, etc. of the pig are not particularly limited and may be appropriately selected depending on the intended purpose.

The type of the pig is also not particularly limited and may be appropriately selected depending on the intended purpose. The pig is preferably the above-described extremely small-size miniature pig from the viewpoint of easy handling as an experimental animal.

<Monkey>

The type, body weight, age, sex, etc. of the monkey are not particularly limited and may be appropriately selected depending on the intended purpose.

<Guinea Pig>

The type, body weight, age, sex, etc. of the guinea pig are not particularly limited and may be appropriately selected depending on the intended purpose.

The atrioventricular block model is preferably a model obtained by administering an immune regulator targeting a sphingosine-1-phosphate receptor to the pig, the monkey or the guinea pig.

<Applications>

The atrioventricular block model can suitably be used for, for example, analysis of pathological condition of atrioventricular block.

(Method for Producing Atrioventricular Block Model)

A method of the present invention for producing an atrioventricular block model includes: an administering step; and, if necessary, further includes other steps such as an anesthetizing step.

<Administering Step>

The administering step is a step of administering an immune regulator targeting a sphingosine-1-phosphate receptor to an animal selected from a pig, a monkey and a guinea pig.

The body weight, age, sex, etc. of the pig are not particularly limited and may be appropriately selected depending on the intended purpose.

The type of the pig is also not particularly limited and may be appropriately selected depending on the intended purpose. The pig is preferably the above-described extremely small-size miniature pig from the viewpoint of easy handling as an experimental animal.

The type, body weight, age, sex, etc. of the monkey are not particularly limited and may be appropriately selected depending on the intended purpose.

The type, body weight, age, sex, etc. of the guinea pig are not particularly limited and may be appropriately selected depending on the intended purpose.

The immune regulator is not particularly limited and may be appropriately selected depending on the intended purpose so long as it targets a sphingosine-1-phosphate receptor. Examples thereof include those listed for the administrating step of the method for allowing an animal to develop atrioventricular block.

A method for administering the immune regulator is not particularly limited and may be appropriately selected depending on the intended purpose, but is preferably intravenous administration.

A dose of the immune regulator is not particularly limited and may be appropriately selected depending on the intended purpose.

When the immune regulator is fingolimod, the dose thereof is preferably at least 0.1 mg/kg. When the dose is less than 0.1 mg/kg, there may be a case where atrioventricular block is not developed.

When the immune regulator is siponimod, the dose thereof is preferably at least 0.01 mg/kg. When the dose is less than 0.01 mg/kg, there may be a case where atrioventricular block is not developed.

<Anesthetizing Step>

The anesthetizing step is a step of anesthetizing a pig, a monkey or a guinea pig. The anesthetizing step is preferably performed before the administering step. The anesthetizing step can be performed in the same manner as in the anesthetizing step of the method for allowing a pig, a monkey or a guinea pig to develop atrioventricular block.

the extremely small-size miniature pigs (n=2) of Example 1 for 10 min at a dose of 0.1 mg/kg. An electrocardiogram was recorded for 60 min from the start of administration of the FTY720 solution.

Notably, since the clinically recommended dose of FTY720 in Japan is 0.5 mg (oral administration/individual/day), the dose of 0.1 mg/kg is a sufficient amount.

<Results>

Figure 1B:
FIG. 1B shows one exemplary trace of an electrocardiogram of a pig at 10 min after the start of drug administration (0.1 mg/kg/10 min) to the pig in Test Example 1.
Figure 1C:
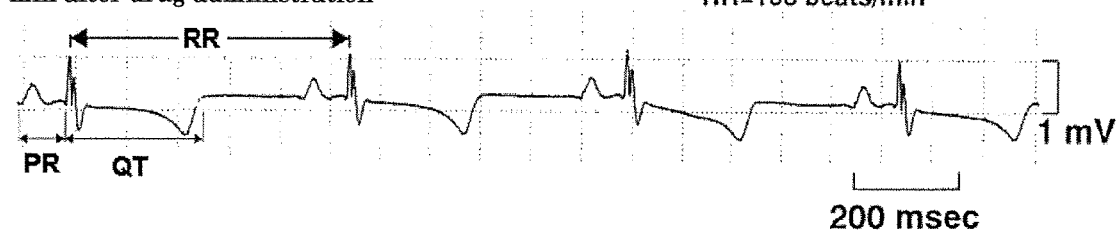
FIG. 1C shows one exemplary trace of an electrocardiogram of a pig at 60 min after the start of drug administration (0.1 mg/kg/10 min) to the pig in Test Example 1.

FIG. 1A shows one exemplary trace of an electrocardiogram of evaluation of base control (before drug administration). FIG. 1B shows one exemplary trace of an electrocardiogram at 10 min after the start of administration of FTY720. FIG. 1C shows one exemplary trace of an electrocardiogram at 60 min after the start of administration of FTY720. Notably, from FIGS. 1A to 1C, heart rate (HR), PR interval, QT interval and RR interval are shown in the following Table 1, where #1 and #2 refer to each individual.

TABLE 1

|  | Individual | Heart rate (HR) [beats/min] | PR interval [ms] | QT interval [ms] | RR interval [ms] |
| --- | --- | --- | --- | --- | --- |
| Evaluation of base control | #1 | 144 | 78 | 250 | 417 |
|  | #2 | 191 | 70 | 222 | 316 |
| 10 min after the administration of the drug | #1 | 137 | 78 | 271 | 438 |
|  | #2 | 192 | 71 | 221 | 311 |
| 60 min after the administration of the drug | #1 | 108 | 89 | 271 | 552 |
|  | #2 | 197 | 75 | 227 | 304 |

EXAMPLES

The present invention will next be described in detail by way of Examples, which should not be construed as limiting the present invention thereto.

Example 1

Extremely small-size miniature pigs (trade name: Micro-minipig, body weight: about 10 kg, male, obtained from Fuji Micra Inc.) were each anesthetized by allowing them to inhale 100% by volume oxygen and 4% by volume vaporized halothane (product of Takeda Pharmaceutical Company Limited.). After insertion of a tracheal cannula, an artificial respirator was used to ventilate it with 100% by volume oxygen and 1% by volume vaporized halothane. Here, the artificial respirator for experimental animals was set to a tidal volume of 10 mL/kg and a respiration rate of 20 strokes/min. Next, a cannula for drug administration was inserted to their left femoral vein. Then, ECG standard limb II leads was continuously recorded.

Test Example 1

Evaluation of Base Control

Each of the extremely small-size miniature pigs (n=2) of Example 1 was recorded for an electrocardiogram before drug administration.

—Drug Administration—

Fingolimod (FTY720, product of Sigma-Aldrich Inc.) was dissolved in physiological saline (product of Otsuka Pharmaceutical Factory, Inc.) so as to have a concentration of 0.1 mg/mL.

After the evaluation of base control, the cannula for drug administration was inserted, and the above-prepared FTY720 solution was intravenously administered to each of FIGS. 1A to 1C and Table 1 indicate that prolongation of QT interval was observed at 10 min after the administration of FTY720. At 60 min after the administration of FTY720, prolongation of PR interval was also observed.

It is found from these results that the extremely small-size miniature pig can be used as a model for evaluating development of atrioventricular block caused by an immune regulator targeting a sphingosine-1-phosphate receptor, especially development of first-degree atrioventricular block.

Example 2

Monkeys (*Macaca fascicularis*, body weight: about 3 kg, male, produced in China, purchased from a domestic breeder) were each anesthetized by intravenously administering thereto sodium thiopental (product of Mitsubishi Tanabe Pharma Corporation) at 25 mg/kg. After insertion of a tracheal cannula, an artificial respirator was used to ventilate it with 100% by volume oxygen and 1% by volume vaporized halothane. Here, the artificial respirator for experimental animals was set to a tidal volume of 20 mL/kg and a respiration rate of 15 strokes/min. Next, a cannula for drug administration was inserted to their left femoral vein. Then, ECG standard limb II leads was continuously recorded.

Test Example 2

Evaluation of Base Control

Each of the monkeys (n=2) of Example 2 was recorded for an electrocardiogram before drug administration.

—Drug Administration—

Fingolimod (FTY720, product of Sigma-Aldrich Inc.) was dissolved in physiological saline (product of Otsuka Pharmaceutical Factory, Inc.) so as to have a concentration of 0.1 mg/mL.

After the evaluation of base control, the cannula for drug administration was inserted, and the above-prepared FTY720 solution was intravenously administered to each of the monkeys (n=2) of Example 2 for 10 min at a dose of 0.1 mg/kg. An electrocardiogram was recorded for 60 min from the start of administration of the FTY720 solution.

<Results>

Figure 2A:
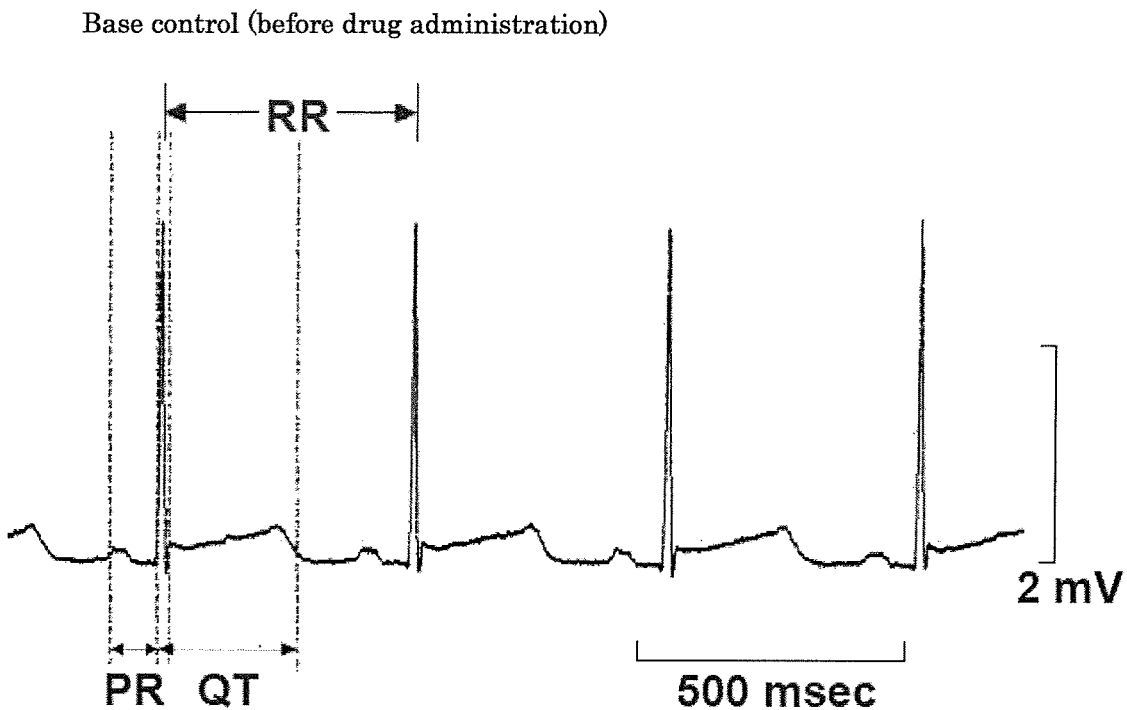
FIG. 2A shows one exemplary trace of an electrocardiogram of a monkey before drug administration in Test Example 2.
Figure 2B:
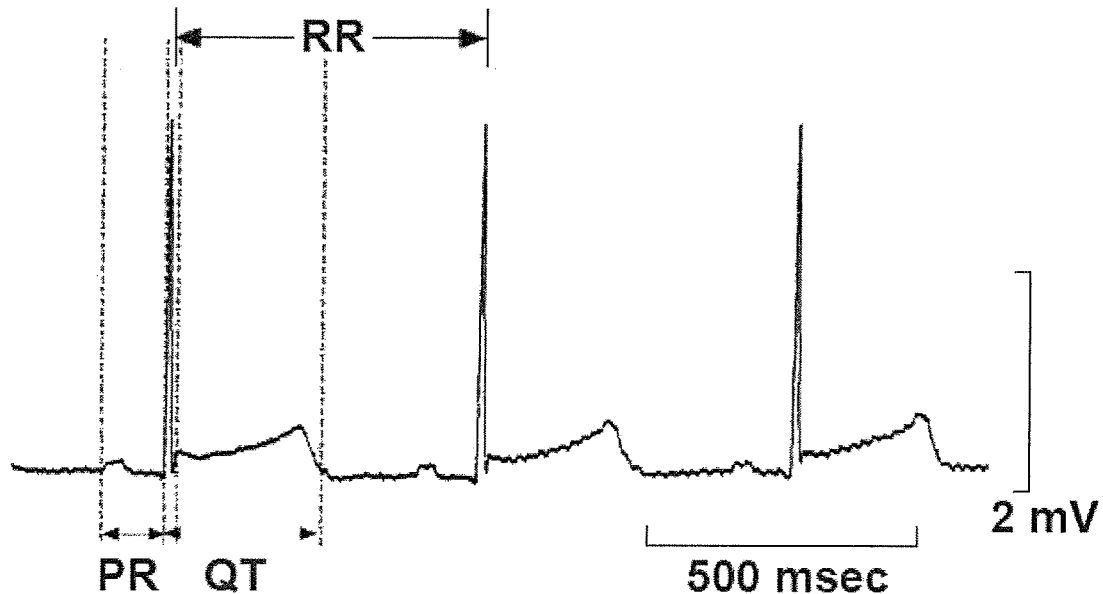
FIG. 2B shows one exemplary trace of an electrocardiogram of a monkey at 50 min after the start of drug administration (0.1 mg/kg/10 min) to the monkey in Test Example 2.

FIG. 2A shows one exemplary trace of an electrocardiogram of evaluation of base control (before drug administration). FIG. 2B shows one exemplary trace of an electrocardiogram at 50 min after the start of administration of FTY720. Notably, from FIGS. 2A and 2B, heart rate (HR) and PR interval are shown in the following Table 2, where #1 and #2 refer to each individual.

TABLE 2

| | Individual | Heart rate (HR) [beats/min] | PR interval [ms] |
|---|---|---|---|
| Evaluation of base control | #1 | 130 | 65 |
| | #2 | 127 | 92 |
| 50 min after the administration of the drug | #1 | 105 | 71 |
| | #2 | 104 | 110 |

FIGS. 2A and 2B and Table 2 indicate that prolongation of PR interval was observed at 50 min after the administration of the drug.

It is found from these results that the monkey can be used as a model for evaluating development of atrioventricular block caused by an immune regulator targeting a sphingosine-1-phosphate receptor, especially development of first-degree atrioventricular block.

Example 3

Guinea pigs (Hartley, body weight: 420 g to 650 g, male, obtained from Japan SLC, Inc.) were each anesthetized by intraperitoneally administering thereto sodium thiopental (product of Mitsubishi Tanabe Pharma Corporation) at 50 mg/kg. Next, a tracheal cannula was inserted into each of the guinea pigs. While their body temperature was being maintained at 37° C. with a warming pad, the guinea pigs were allowed to inhale 100% by volume oxygen and 1% by volume vaporized halothane (product of Takeda Pharmaceutical Company Limited.) using an artificial respirator for experimental animals (SN-480-7; product of shimano Co., Ltd.). Here, the artificial respirator for experimental animals was set to a tidal volume of 10 mL/kg and a respiration rate of 60 strokes/min. Next, a cannula for drug administration was inserted to their left femoral vein. In addition, a heparinized catheter for monitoring the blood pressure was inserted to the aorta through the left femoral vein. Then, ECG standard limb II leads was continuously recorded.

Test Example 3-1

Evaluation of Base Control

Each of the guinea pigs (n=12) of Example 3 was recorded for an electrocardiogram before administration of a drug or a solvent.

—Low-Dose Drug Administration Group—

FTY720 (product of Sigma-Aldrich Inc.) was dissolved in physiological saline (product of Otsuka Pharmaceutical Factory, Inc.) so as to have a concentration of 0.03 mg/mL.

After the evaluation of base control, the cannula for drug administration was inserted, and the above-prepared FTY720 solution was intravenously administered to each of the guinea pigs (n=4) of Example 3 for 10 min at a dose of 0.01 mg/kg. These guinea pigs were evaluated for parameters by the following evaluation methods at 5 min, 10 min, 15 min, 20 min, 30 min, 45 min or 60 min after the administration of the FTY720 solution.

—High-Dose Drug Administration Group—

FTY720 (product of Sigma-Aldrich Inc.) was dissolved in physiological saline (product of Otsuka Pharmaceutical Factory, Inc.) so as to have a concentration of 0.3 mg/mL.

After the evaluation of base control, the cannula for drug administration was inserted, and the above-prepared FTY720 solution was intravenously administered to each of the guinea pigs (n=4) of Example 3 for 10 min at a dose of 0.1 mg/kg. These guinea pigs were evaluated for parameters by the following evaluation methods at 5 min, 10 min, 15 min, 20 min, 30 min, 45 min or 60 min after the administration of the FTY720 solution.

—Solvent Administration Group—

After the evaluation of base control, the cannula for drug administration was inserted, and physiological saline containing no FTY720 was intravenously administered to each of the guinea pigs of Example 3 for 10 min at a dose of 0.33 mL/kg. These guinea pigs were evaluated for parameters by the following evaluation methods at 5 min, 10 min, 15 min, 20 min, 30 min, 45 min or 60 min after the administration of the physiological saline.

<Evaluation Method>

The aortic pressure and the electrocardiogram were monitored using a polygraph system (RM-6000, product of NIHON KOHDEN Co. Ltd.) and analyzed with a full-automated analysis system in real time (WinVAS ver. 3, 1.1R03; product of Physio-Tech Co., Ltd.).

Parameters of the electrocardiogram were measured three times, and the obtained values were averaged. Atrial rate was calculated from PP interval of the electrocardiogram. Ventricular rate was calculated from RR interval of the electrocardiogram.

<Results>

Figure 3A:
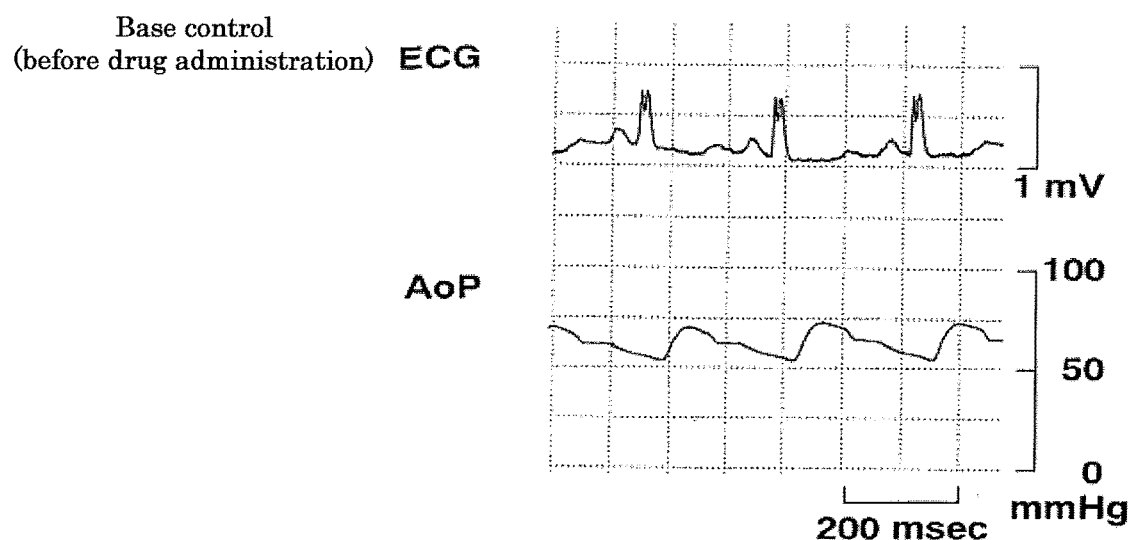
FIG. 3A shows exemplary traces of an electrocardiogram and an aortic pressure of a guinea pig before drug administration in Test Example 3-1.
Figure 3B:
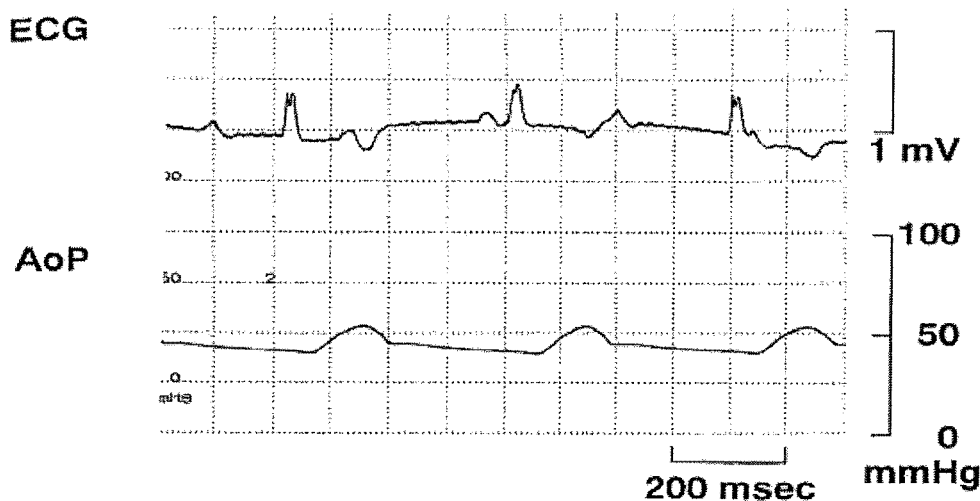
FIG. 3B shows exemplary traces of an electrocardiogram and an aortic pressure of a guinea pig at 45 min after the start of high-dose drug administration (0.1 mg/kg/10 min) to the guinea pig in Test Example 3-1.

FIG. 3A shows exemplary traces of an electrocardiogram (ECG) and an aortic pressure (AoP) in the evaluation of base control (before administration of the drug). FIG. 3B shows exemplary traces of an electrocardiogram (ECG) and an aortic pressure (AoP) at 45 min after the start of the high-dose administration of FTY720.

FIG. 3A illustrates that P wave and R wave correspond to each other in the electrocardiogram before administration of the drug and show normal PR interval. In contrast, FIG. 3B illustrates that P wave and R wave do not correspond to each other in the electrocardiogram at 45 min after the start of the high-dose administration. That is, it has been confirmed in the high-dose FTY720 administration group that the atrium and the ventricle are contracted independently of each other at their own individual rhythms.

Figure 4A:
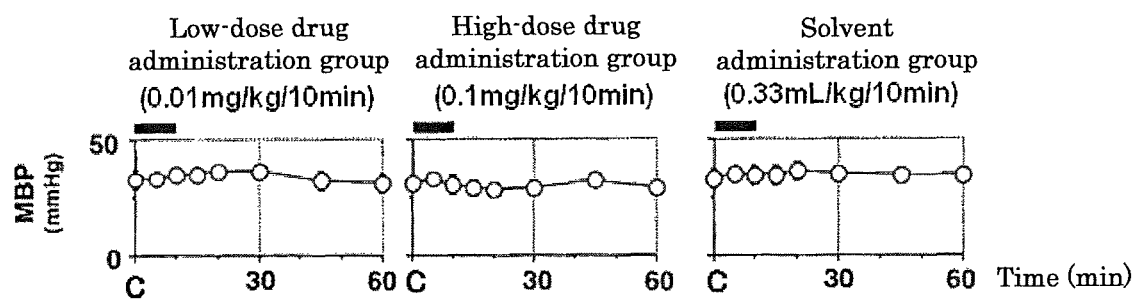
FIG. 4A shows mean blood pressure (MBP) in a low-dose drug administration group (0.01 mg/kg/10 min), a high-dose drug administration group (0.1 mg/kg/10 min) and a solvent administration group of a guinea pig in Test Example 3-1.
Figure 4B:
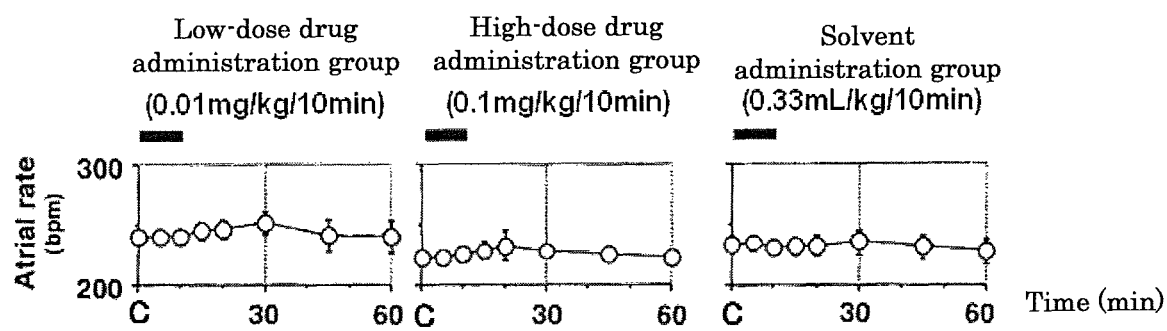
FIG. 4B shows atrial rate in a low-dose drug administration group (0.01 mg/kg/10 min), a high-dose drug administration group (0.1 mg/kg/10 min) and a solvent administration group of a guinea pig in Test Example 3-1.
Figure 4C:
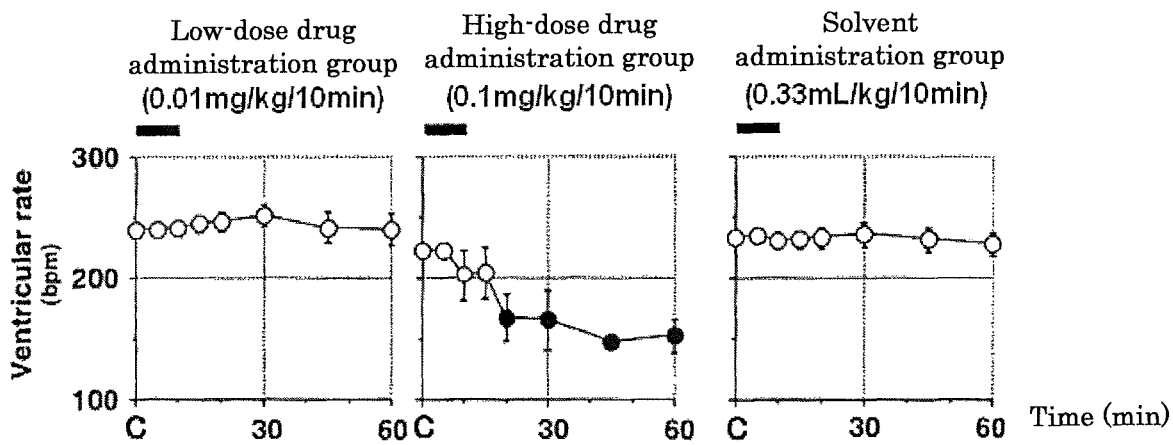
FIG. 4C shows ventricular rate in a low-dose drug administration group (0.01 mg/kg/10 min), a high-dose drug administration group (0.1 mg/kg/10 min) and a solvent administration group of a guinea pig in Test Example 3-1.
Figure 4D:
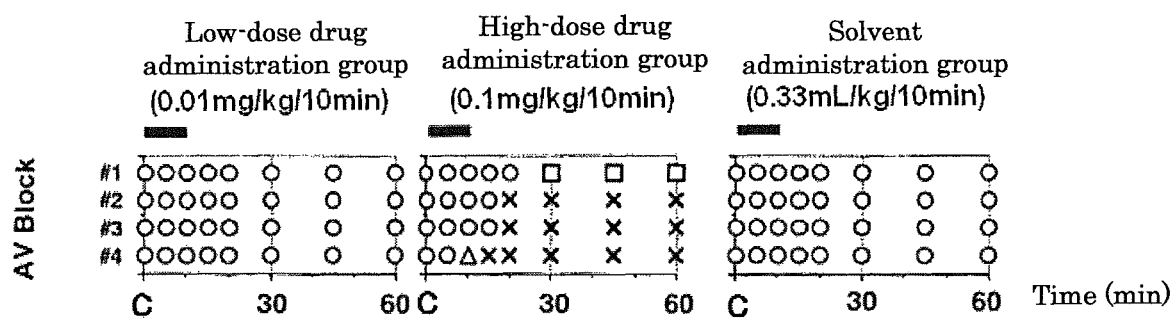
FIG. 4D shows presence or absence of development of atrioventricular block (AV Block) in a low-dose drug administration group (0.01 mg/kg/10 min), a high-dose drug administration group (0.1 mg/kg/10 min) and a solvent administration group of a guinea pig in Test Example 3-1.
Figure 4E:
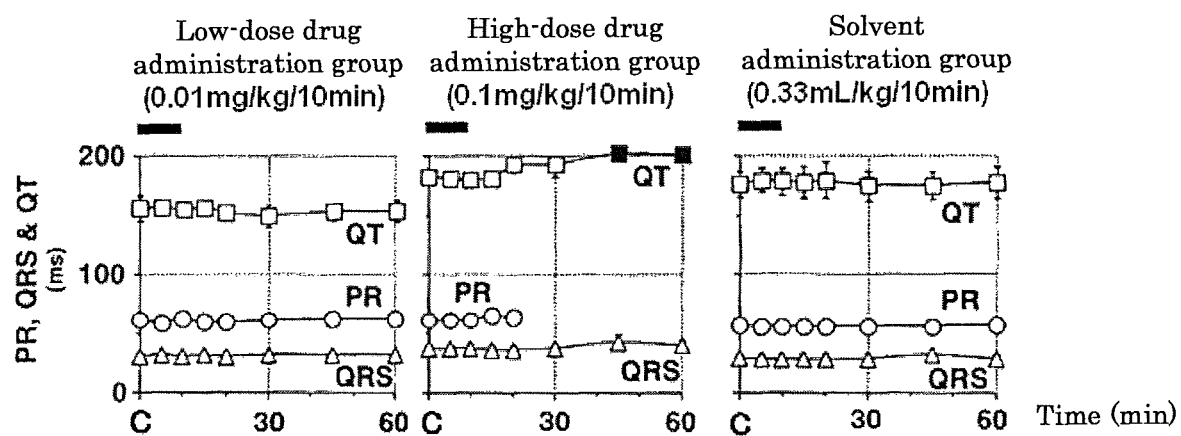
FIG. 4E shows PR interval, QRS width and QT interval in a low-dose drug administration group (0.01 mg/kg/10 min), a high-dose drug administration group (0.1 mg/kg/10 min) and a solvent administration group of a guinea pig in Test Example 3-1.

FIG. 4A shows mean blood pressure (MBP), FIG. 4B shows atrial rate, FIG. 4C shows ventricular rate, FIG. 4D shows presence or absence of development of atrioventricular block (AV Block) and its type, and FIG. 4E shows PR interval, QRS width and QT interval.

The measurements in FIGS. 4A to 4E are expressed as mean±SE (n=4). The difference between the parameters was evaluated with one-way repeated measures analysis of variance (ANOVA). It was considered that $p<0.05$ is statistically significant. In FIG. 4A to 4C and FIG. 4E, "white circle," "white square" and "white triangle" each mean absence of a significant difference relative to the value of the evaluation of base control (C), and "black circle" and "black square"

each mean presence of a significant difference relative to the value of the evaluation of base control (C).

Also, in FIG. 4D, "white circle" means absence of development of atrioventricular block or presence of development of first-degree atrioventricular block, "white square" means presence of development of second-degree atrioventricular block (Wenckebach type), "white triangle" means presence of development of advanced atrioventricular block, "x-mark" means presence of development of third-degree atrioventricular block (complete atrioventricular block), and #1 to 4 refer to each individual.

It has been found from FIGS. 4A to 4E that since no significant change was observed at each point of time before and after the administration of physiological saline in the solvent administration group, physiological saline of 0.33 mL/kg did not affect the present evaluation system. In addition, no statistically significant difference was observed between each parameter in the low-dose FTY720 administration group and the high-dose FTY720 administration group before the administration of FTY720 and each parameter in the solvent administration group before the administration of solvent.

The following Table 3 shows blood pressure and atrial rate in the evaluation of base control (C) before the administration of FTY720. As shown in FIGS. 4A and 4B, no significant change in blood pressure and atrial rate was observed for 60 min from the start of the administration of FTY720.

TABLE 3

| | Evaluation of base control | |
|---|---|---|
| | Blood pressure (MBP) [mmHg] | Atrial rate [bpm] |
| Low-dose FTY720 administration group | 31 ± 2 | 239 ± 6 |
| High-dose FTY720 administration group | 33 ± 4 | 222 ± 4 |

As shown in FIG. 4C, the ventricular rate before the start of the administration of FTY720 or the solvent was almost the same value among the solvent administration group, the low-dose FTY720 administration group, and the high-dose FTY720 administration group.

For 60 min from the start of the administration, no significant change in ventricular rate was observed in the low-dose FTY720 administration group. In contrast, in the high-dose FTY720 administration group, a significant decrease in ventricular rate was observed from 20 min to 60 min for which complete atrioventricular block developed.

As shown in FIG. 4D, three individuals out of the four individuals in the high-dose FTY720 administration group developed complete atrioventricular block, and one individual developed Wenckebach-type atrioventricular block.

The following Table 4 shows PR interval, QRS width and QT interval in the evaluation of base control (C) before administration of FTY720.

TABLE 4

| | Evaluation of base control | | |
|---|---|---|---|
| | PR interval [ms] | QRS interval [ms] | QT interval [ms] |
| Low-dose FTY720 administration group | 61 ± 6 | 30 ± 2 | 155 ± 10 |

TABLE 4-continued

| | Evaluation of base control | | |
|---|---|---|---|
| | PR interval [ms] | QRS interval [ms] | QT interval [ms] |
| High-dose FTY720 administration group | 60 ± 2 | 37 ± 3 | 182 ± 4 |

It has been found from FIG. 4E that no significant change in any electrophysiological parameters was observed in the low-dose FTY720 administration group at 60 min from the start of the administration. In contrast, in the high-dose FTY720 administration group, although no significant change in QRS width was observed, the PR interval was prolonged before development of atrioventricular block. Also, the QT interval was prolonged from 45 min to 60 min.

It is found from these results that the guinea pig can be used as a model for evaluating development of atrioventricular block caused by an immune regulator targeting a sphingosine-1-phosphate receptor, especially development of complete atrioventricular block.

Test Example 3-2

Evaluation of Base Control

Each of the guinea pigs (n=12) of Example 3 was recorded for an electrocardiogram before administration of a drug or a solvent.
—Low-Dose Drug Administration Group—
BAF312 (product of Meiji Seika Pharma Co., Ltd.) was dissolved in dimethyl sulfoxide (hereinafter may be referred to as "DMSO"; product of Sigma-Aldrich Inc.) so as to have a concentration of 0.003 mg/mL.
After the evaluation of base control, the cannula for drug administration was inserted, and the above-prepared BAF312 solution was intravenously administered to each of the guinea pigs (n=4) of Example 3 for 10 min at a dose of 0.001 mg/kg. These guinea pigs were evaluated for parameters by the following evaluation methods at 5 min, 10 min, 15 min, 20 min, 30 min, 45 min or 60 min after the administration of the BAF312 solution.
—High-Dose Drug Administration Group—
BAF312 (product of Meiji Seika Pharma Co., Ltd.) was dissolved in DMSO (product of Sigma-Aldrich Inc.) so as to have a concentration of 0.03 mg/mL.
After the evaluation of base control, the cannula for drug administration was inserted, and the above-prepared BAF312 solution was intravenously administered to each of the guinea pigs (n=4) of Example 3 for 10 min at a dose of 0.01 mg/kg. These guinea pigs were evaluated for parameters by the following evaluation methods at 5 min, 10 min, 15 min, 20 min, 30 min, 45 min or 60 min after the administration of the BAF312 solution.
—Solvent Administration Group—
After the evaluation of base control, the cannula for drug administration was inserted, and DMSO containing no BAF312 was intravenously administered to each of the guinea pigs of Example 3 for 10 min at a dose of 0.33 mL/kg. These guinea pigs were evaluated for parameters by the following evaluation methods at 5 min, 10 min, 15 min, 20 min, 30 min, 45 min or 60 min after the administration of the physiological saline.
<Evaluation Method>
The aortic pressure and the electrocardiogram were monitored using a polygraph system (RM-6000, product of NIHON KOHDEN Co. Ltd.) and analyzed with a full-automated analysis system in real time (WinVAS ver. 3, 1.1R03; product of Physio-Tech Co., Ltd).

Parameters of the electrocardiogram were measured three times, and the obtained values were averaged. Atrial rate was calculated from PP interval of the electrocardiogram. Ventricular rate was calculated from RR interval of the electrocardiogram.

<Results>

Figure 5A:
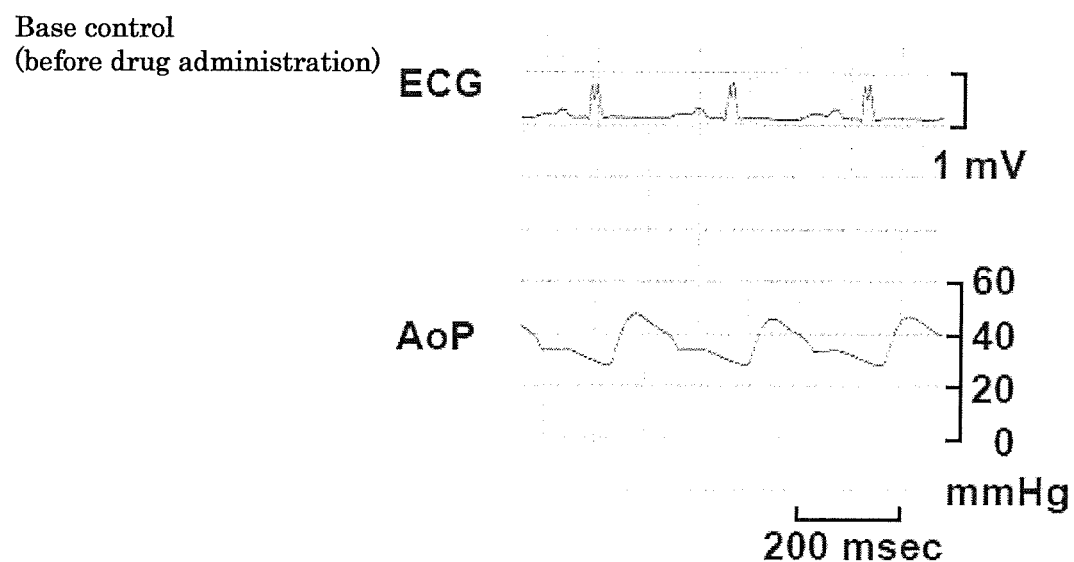
FIG. 5A shows exemplary traces of an electrocardiogram and an aortic pressure of a guinea pig before drug administration in Test Example 3-2.
Figure 5B:
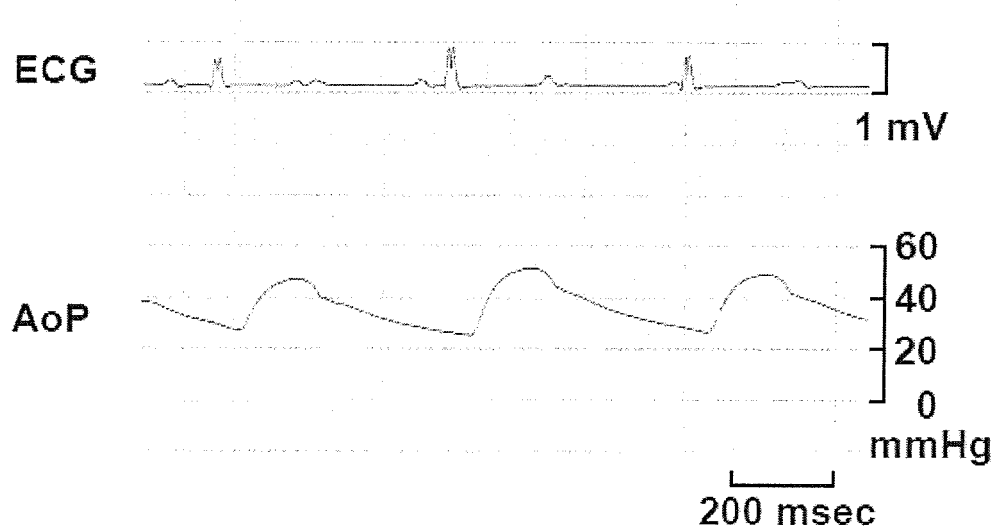
FIG. 5B shows exemplary traces of an electrocardiogram and an aortic pressure of a guinea pig at 45 min after the start of high-dose drug administration (0.01 mg/kg/10 min) to the guinea pig in Test Example 3-2.

FIG. 5A shows exemplary traces of an electrocardiogram (ECG) and an aortic pressure (AoP) in the evaluation of base control (before administration of the drug). FIG. 5B shows exemplary traces of an electrocardiogram (ECG) and an aortic pressure (AoP) at 45 min after the start of the high-dose administration of BAF312.

FIG. 5A illustrates that P wave and R wave correspond to each other in the electrocardiogram before administration of the drug and show normal PR interval. In contrast, FIG. 5B illustrates that P wave and R wave do not correspond to each other in the electrocardiogram at 45 min after the start of the high-dose administration. That is, it has been confirmed in the high-dose BAF312 administration group that the atrium and the ventricle are contracted independently of each other at their own individual rhythms.

Figure 6A:
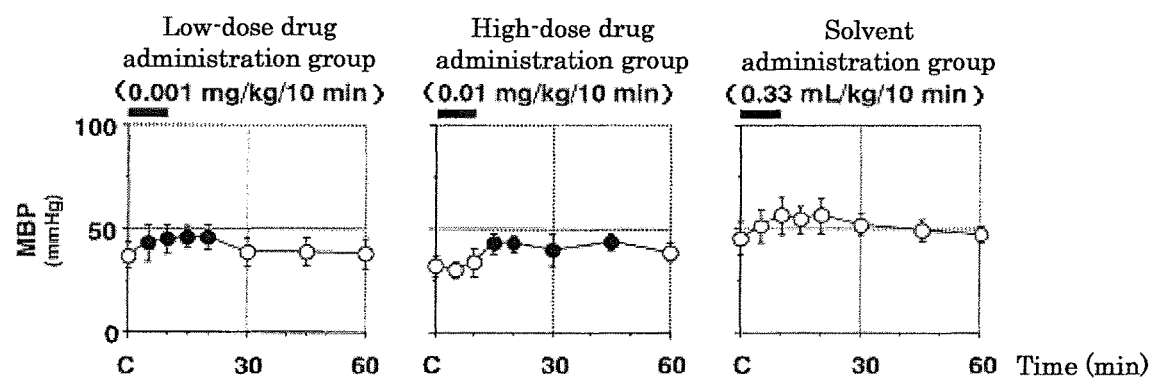
FIG. 6A shows mean blood pressure (MBP) in a low-dose drug administration group (0.001 mg/kg/10 min), a high-dose drug administration group (0.01 mg/kg/10 min) and a solvent administration group of a guinea pig in Test Example 3-2.
Figure 6B:
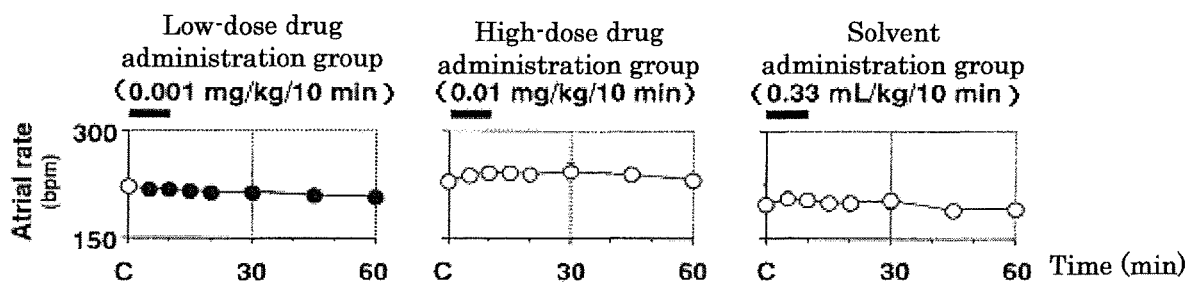
FIG. 6B shows atrial rate in a low-dose drug administration group (0.001 mg/kg/10 min), a high-dose drug administration group (0.01 mg/kg/10 min) and a solvent administration group of a guinea pig in Test Example 3-2.
Figure 6C:
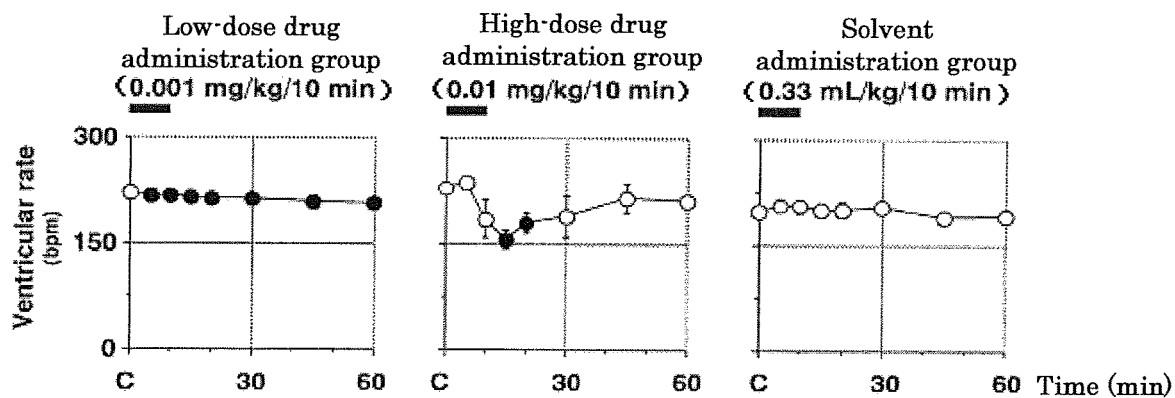
FIG. 6C shows ventricular rate in a low-dose drug administration group (0.001 mg/kg/10 min), a high-dose drug administration group (0.01 mg/kg/10 min) and a solvent administration group of a guinea pig in Test Example 3-2.
Figure 6D:
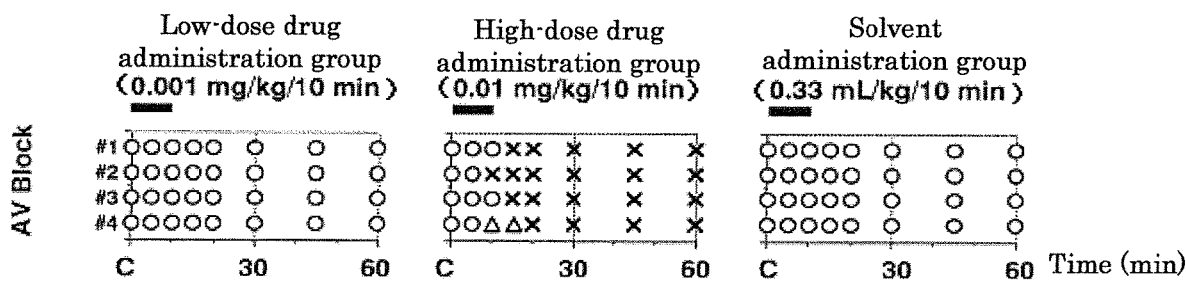
FIG. 6D shows presence or absence of development of atrioventricular block (AV Block) in a low-dose drug administration group (0.001 mg/kg/10 min), a high-dose drug administration group (0.01 mg/kg/10 min) and a solvent administration group of a guinea pig in Test Example 3-2.
Figure 6E:
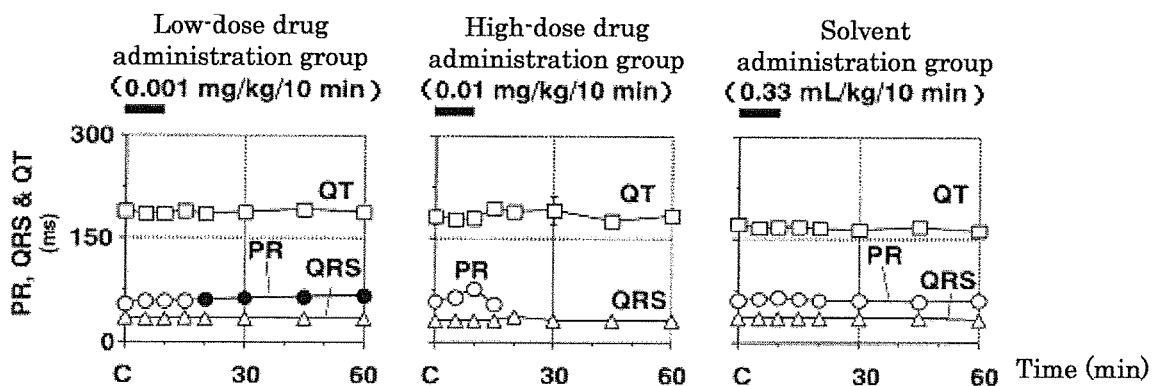
FIG. 6E shows PR interval, QRS width and QT interval in a low-dose drug administration group (0.001 mg/kg/10 min), a high-dose drug administration group (0.01 mg/kg/10 min) and a solvent administration group of a guinea pig in Test Example 3-2.

FIG. 6A shows mean blood pressure (MBP), FIG. 6B shows atrial rate, FIG. 6C shows ventricular rate, FIG. 6D shows presence or absence of development of atrioventricular block (AV Block) and its type, and FIG. 6E shows PR interval, QRS width and QT interval.

The measurements in FIGS. 6A to 6E are expressed as mean±SE (n=4). The difference between the parameters was evaluated with one-way repeated measures analysis of variance (ANOVA). It was considered that $p<0.05$ is statistically significant. In FIG. 6A to 6C and FIG. 6E, "white circle," "white square" and "white triangle" each mean absence of a significant difference relative to the value of the evaluation of base control (C), and "black circle" means presence of a significant difference relative to the value of the evaluation of base control (C).

Also, in FIG. 6D, "white circle" means absence of development of atrioventricular block or presence of development of first-degree atrioventricular block, "white triangle" means presence of development of advanced atrioventricular block, "x-mark" means presence of development of third-degree atrioventricular block (complete atrioventricular block), and #1 to 4 refer to each individual.

It has been found from FIGS. 6A to 6E that since no significant change was observed at each point of time before and after the administration of physiological saline in the solvent administration group, physiological saline of 0.33 mL/kg did not affect the present evaluation system. In addition, no statistically significant difference was observed between each parameter in the low-dose BAF312 administration group and the high-dose BAF312 administration group before the administration of BAF312 and each parameter in the solvent administration group before the administration of solvent.

The following Table 5 shows blood pressure and atrial rate in the evaluation of base control (C) before the administration of BAF312. As shown in FIG. 6A, an increase in blood pressure was observed in the low-dose BAF312 administration group and the high-dose BAF312 administration group. Also, as shown in FIG. 6B, a decrease in atrial rate was observed in the low-dose BAF312 administration group, while no significant change in atrial rate was observed in the high-dose BAF312 administration group.

TABLE 5

| | Evaluation of base control | |
|---|---|---|
| | Blood pressure (MBP) [mmHg] | Atrial rate [bpm] |
| Low-dose BAF312 administration group | 37 ± 6 | 221 ± 7 |
| High-dose BAF312 administration group | 32 ± 5 | 229 ± 7 |

As shown in FIG. 6C, the ventricular rate before the start of the administration of BAF312 or the solvent was almost the same value among the solvent administration group, the low-dose BAF312 administration group, and the high-dose BAF312 administration group.

From 5 min to 60 min from the start of the administration, a decrease in atrial rate and ventricular rate was observed in the low-dose BAF312 administration group. In contrast, in the high-dose BAF312 administration group, a decrease in ventricular rate was observed from 10 min to 15 min from the start of the administration.

As shown in FIG. 6D, all of the four individuals in the high-dose BAF312 administration group developed complete atrioventricular block.

The following Table 6 shows PR interval, QRS width and QT interval in the evaluation of base control (C) before administration of BAF312.

TABLE 6

| | Evaluation of base control | | |
|---|---|---|---|
| | PR interval [ms] | QRS interval [ms] | QT interval [ms] |
| Low-dose BAF312 administration group | 56 ± 2 | 35 ± 3 | 188 ± 5 |
| High-dose BAF312 administration group | 59 ± 3 | 31 ± 0 | 182 ± 10 |

As shown in FIG. 6E, in the low-dose BAF312 administration group, no significant change in QT interval or QRS width was observed but prolongation of PR interval was observed. Meanwhile, in the high-dose BAF312 administration group, no significant change in QT interval or QRS width was observed but PR interval was prolonged before development of atrioventricular block.

It is also found from these results that the guinea pig can be used as a model for evaluating development of atrioventricular block caused by an immune regulator targeting a sphingosine-1-phosphate receptor, especially development of complete atrioventricular block. Furthermore, BAF312 can also be used as the immune regulator.

Comparative Example 1

Dogs (body weight: 10 kg, male, obtained from Nosan Co., Ltd.) were each anesthetized by intravenously administering thereto sodium thiopental (product of Mitsubishi Tanabe Pharma Corporation) at 30 mg/kg. After insertion of a tracheal cannula, an artificial respirator was used to ventilate it with 100% by volume oxygen and 1% by volume vaporized halothane. Here, the artificial respirator for experimental animals was set to a tidal volume of 20 mL/kg and a respiration rate of 15 strokes/min. Next, a cannula for drug administration was inserted to their left femoral vein. Then, ECG standard limb II leads was continuously recorded.

Comparative Test Example 1

Evaluation of Base Control

Each of the dogs (n=4) of Comparative Example 1 was recorded for an electrocardiogram before drug administration.
—Low-Dose Drug Administration Group—
Fingolimod (FTY720, product of Sigma-Aldrich Inc.) was dissolved in 1% by mass lactic acid solution (product of Otsuka Pharmaceutical Factory, Inc.) so as to have a concentration of 0.3 mg/mL.
After the evaluation of base control, the cannula for drug administration was inserted, and the above-prepared FTY720 solution was intravenously administered to each of the dogs (n=4) of Comparative Example 1 for 10 min at a dose of 0.3 mg/kg. An electrocardiogram was recorded for 30 min from the start of administration of the FTY720 solution.
—High-Dose Drug Administration Group—
Fingolimod (FTY720, product of Sigma-Aldrich Inc.) was dissolved in 1% by mass lactic acid solution (product of Otsuka Pharmaceutical Factory, Inc.) so as to have a concentration of 3 mg/mL.
After the evaluation of base control, the cannula for drug administration was inserted, and the above-prepared FTY720 solution was intravenously administered to each of the dogs (n=4) of Comparative Example 1 for 10 min at a dose of 3 mg/kg. An electrocardiogram was recorded for 30 min from the start of administration of the FTY720 solution.
<Results>
In the low-dose FTY720 administration group, no significant change was observed in heart rate (HR) and PR interval. In the high-dose FTY720 administration group, the HR was significantly increased but no change in PR interval was observed.

These results indicate that a dog cannot be used as a model for evaluating atrioventricular block caused by an immune regulator targeting a sphingosine-1-phosphate receptor. That is, as shown in Test Examples 1 to 3-2, it has been found that the evaluation of atrioventricular block is possible specifically in a pig, a monkey or a guinea pig.

Aspects of the present invention are, for example, as follows.
<1> A pig for an atrioventricular block model,
wherein the pig is used for production of an atrioventricular block model.
<2> The pig for an atrioventricular block model according to <1>,
wherein the pig is anesthetized with halothane.
<3> A monkey for an atrioventricular block model,
wherein the monkey is used for production of an atrioventricular block model.
<4> The monkey for an atrioventricular block model according to <3>,
wherein the monkey is anesthetized with halothane.
<5> A guinea pig for an atrioventricular block model,
wherein the guinea pig is used for production of an atrioventricular block model.
<6> The guinea pig for an atrioventricular block model according to <5>,
wherein the guinea pig is anesthetized with halothane.
<7> A method for allowing an animal to develop atrioventricular block, the method including:
administering an immune regulator targeting a sphingosine-1-phosphate receptor to an animal selected from a pig, a monkey and a guinea pig.
<8> The method for allowing an animal to develop atrioventricular block according to <7>,
wherein the animal is a pig.
<9> The method for allowing an animal to develop atrioventricular block according to <8>, further including: anesthetizing the pig with halothane.
<10> The method for allowing an animal to develop atrioventricular block according to <7>,
wherein the animal is a monkey.
<11> The method for allowing an animal to develop atrioventricular block according to <10>, further including: anesthetizing the monkey with halothane.
<12> The method for allowing an animal to develop atrioventricular block according to <7>,
wherein the animal is a guinea pig.
<13> The method for allowing an animal to develop atrioventricular block according to <12>, further including: anesthetizing the guinea pig with halothane.
<14> An atrioventricular block model,
wherein the atrioventricular block model is a pig.
<15> The atrioventricular block model according to <14>,
wherein the atrioventricular block model is obtained by administering an immune regulator targeting a sphingosine-1-phosphate receptor to the pig.
<16> An atrioventricular block model,
wherein the atrioventricular block model is a monkey.
<17> The atrioventricular block model according to <16>,
wherein the atrioventricular block model is obtained by administering an immune regulator targeting a sphingosine-1-phosphate receptor to the monkey.
<18> An atrioventricular block model,
wherein the atrioventricular block model is a guinea pig.
<19> The atrioventricular block model according to <18>,
wherein the atrioventricular block model is obtained by administering an immune regulator targeting a sphingosine-1-phosphate receptor to the guinea pig.
<20> A method for producing an atrioventricular block model, the method including:
administering an immune regulator targeting a sphingosine-1-phosphate receptor to an animal selected from a pig, a monkey and a guinea pig.
<21> The method for producing an atrioventricular block model according to <20>,
wherein the animal is a pig.
<22> The method for producing an atrioventricular block model according to <21>, further including: anesthetizing the pig with halothane.
<23> The method for producing an atrioventricular block model according to <20>,
wherein the animal is a monkey.
<24> The method for producing an atrioventricular block model according to <23>, further including: anesthetizing the monkey with halothane.
<25> The method for producing an atrioventricular block model according to <20>,
wherein the animal is a guinea pig.
<26> The method for producing an atrioventricular block model according to <25>, further including: anesthetizing the guinea pig with halothane.
<27> An evaluation method, including:
evaluating development of atrioventricular block caused by an immune regulator targeting a sphingosine-1-phosphate receptor with a pig, a monkey, a guinea pig, or any combination thereof.

<28> The evaluation method according to <27>, wherein the evaluating includes:

primarily evaluating the development of atrioventricular block caused by an immune regulator targeting a sphingosine-1-phosphate receptor with one or both of the pig and the monkey; and secondarily evaluating the development of atrioventricular block caused by an immune regulator targeting a sphingosine-1-phosphate receptor with the guinea pig.

INDUSTRIAL APPLICABILITY

The pig for an atrioventricular block model, the monkey for an atrioventricular block model, and the guinea pig for an atrioventricular block model of the present invention can suitably be used for predicting development of atrioventricular block caused by a drug at the stage of non-clinical trials.

What is claimed is:

1. An evaluation method, comprising:

evaluating development of atrioventricular block caused by fingolimod with a pig, a monkey, a guinea pig, or any combination thereof wherein the evaluating comprises:

administering the fingolimod to one or both of the pig and the monkey, primarily evaluating the development of a first-degree atrioventricular block caused by the fingolimod with one or both of the pig and the monkey as a core battery study;

after the primarily evaluating the development of the first-degree atrioventricular block, administering the fingolimod to the guinea pig, and secondarily evaluating the development of a third-degree atrioventricular block caused by the fingolimod with the guinea pig, wherein the guinea pig is anesthetized with halothane, as a follow-up study to the core battery study.

* * * * *